United States Patent [19]

Singh

[11] Patent Number: 5,260,479

[45] Date of Patent: * Nov. 9, 1993

[54] INHIBITORS OF FARNESYL PROTEIN TRANSFERASE

[75] Inventor: Sheo B. Singh, Edison, N.J.

[73] Assignee: Merck & Co., Inc., Rahway, N.J.

[ * ] Notice: The portion of the term of this patent subsequent to Sep. 14, 2010 has been disclaimed.

[21] Appl. No.: 809,199

[22] Filed: Dec. 16, 1991

[51] Int. Cl.$^5$ .................. C07C 69/34; C07C 69/52; C07C 57/02; C07C 59/235

[52] U.S. Cl. .................................. 560/190; 560/193; 562/595; 554/121

[58] Field of Search ................. 560/190, 193; 562/595; 554/121

[56] References Cited

U.S. PATENT DOCUMENTS 5,043,268  8/1991  Stock .

FOREIGN PATENT DOCUMENTS

0456180A1  11/1991  European Pat. Off. .
WO91/16340  10/1991  PCT Int'l Appl. .

OTHER PUBLICATIONS

Gill, M. "3-[(7)-hexadecenyl]-4-metholfuran-2,5-dione from Piptoporus australienisis.", Phyto Chemistry, 21:1788-1788 (1982).

Turner, W. B., et al., "Secondary metabolites derived from intermediates of the tri-carboxlyic acid cycle", *Fungal metabolites II*, Academic Press, pp. 367-383 (1983).

Biller, S. A., "The first potent inhibitor of squalene synthase: A profound contribution of an ether oxygen to inhibitor—Enzyme Interaction", J. Am. Chem. Soc., 113, 8522-8524 (1991).

Goldstein, J. L., et al., "Non farnesylated tetrapeptide inhibitor of protein farnesyl transferase", *The Journal of Biological Chemistry*, vol. 266, No. 24 pp. 15575-15578 (1991).

Primary Examiner—José G. Dees
Assistant Examiner—Joseph M. Conrad, III
Attorney, Agent, or Firm—Joseph F. DiPrima; Mark R. Daniel; David A. Muthard

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

3 Claims, No Drawings

INHIBITORS OF FARNESYL PROTEIN TRANSFERASE

BACKGROUND OF THE INVENTION

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., *Microbiol. Rev.* 53:171–286 (1989). Forms of Ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Aaa is an aliphatic amino acid, the Xaa is any amino acid) (Willumsen et al., *Nature* 310:583–586 (1984). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., *Cell* 57:1167 (1989); Casey et al., *Proc. Natl. Acad. Sci. USA* 86:8323 (1989)). In addition, Ha-Ras and N-Ras are palmitoylated via formation of a thioester on a Cys residue near a C-terminal Cys farnesyl acceptor (Gutierrez et al., *EMBO J.* 8:1093–1098 (1989); Hancock et al., *Cell* 57: 1167–1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., *J. Biol. Chem.* 263:18236 (1988); Farnsworth et al., *J. Biol. Chem.* 264:20422 (1989)).

Inhibition of Ras farnesylation in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et al., *Cell*, 62: 81–88 (1990); Schaber et al., *J. Biol. Chem.*, 265:14701–14704 (1990); Schafer et al., *Science*, 249: 1133–1139 (1990); Manne et al., *Proc. Natl. Acad. Sci USA*, 87: 7541–7545 (1990)).

Inhibition of farnesyl-protein transferase and, thereby, of farnesylation of the Ras protein, blocks the ability of Ras to transform normal cells to cancer cells. The compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-Aaa$^1$-Aaa$^2$-Xaa box membrane domain present) and activated (impaired GTPase activity, staying bound to GTP) form of Ras acts as a dominant negative Ras inhibitor of membrane-bound Ras function (Gibbs et al., *Proc. Natl. Acad. Sci. USA* 86:6630–6634 (1989)). Cytosol-localized forms of Ras with normal GTPase activity do not act as inhibitors. Gibbs et al., ibid, showed this effect in Xenopus oocytes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects such as interference with other metabolic processes which utilize the enzyme.

These compounds and their analogs are inhibitors of farnesyl-protein transferase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides with the CAAX sequence inhibit Ras farnesylation (Schaber et al., ibid; Reiss et. al., ibid; Reiss et al., *PNAS*, 88:732–736 (1991)). However, the reported inhibitors of farnesyl-transferase are metabolically unstable or inactive in cells.

It has further been reported in the art that a structure of a new citraconic anhydride derivative from *Piptoporous australiensis* has been established by spectroscopic and chemical methods as 3-[(7Z)-hexadecenyl]-4-methylfuran-2,5-dione, (M. Gill, *Phytochemistry*, 21:1786–1788 (1982).

It is, therefore, an object of this invention to develop compounds which will inhibit farnesyl-protein transferase and the farnesylation of the oncogene protein Ras. It is a further object of this invention to develop chemotherapeutic compositions containing the compounds of this invention, and methods for producing the compounds of this invention.

SUMMARY OF THE INVENTION

The present invention includes compounds which inhibit farnesyl-protein transferase and the farnesylation of the oncogene protein Ras, chemotherapeutic compositions containing the compounds of this invention, and methods for producing the compounds of this invention.

The compounds of this invention are illustrated by the formulae:

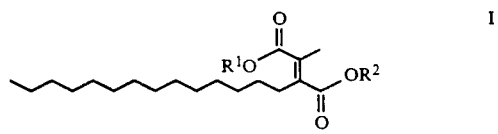

-continued and

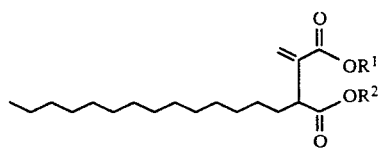

DETAILED DESCRIPTION OF THE INVENTION

The compounds of this invention are useful in the inhibition of farnesyl-protein transferase and the farnesylation of the oncogene protein Ras. In a first embodiment of this invention, the compounds are illustrated by the formula:

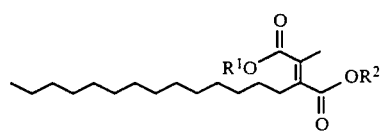

I wherein:
$R^1$ and $R^2$ are each independently selected from:
a) H;
b) $C_{1-5}$alkyl;
c) $C_{1-5}$alkyl substituted with a member of the group consisting of:
  i) phenyl,
  ii) phenyl substituted with methyl, methoxy, halogen (Cl, Br, F, I) or hydroxy; or a pharmaceutically acceptable salt of a compound of formula (I) in which at least one of $R^1$ and $R^2$ is hydrogen;

when $R^1$, $R^2$ is other than H, these compounds may not be inhibitors of farnesyl-protein transferase but may act as prodrugs.

In a second embodiment of this invention, the compounds are illustrated by the formula:

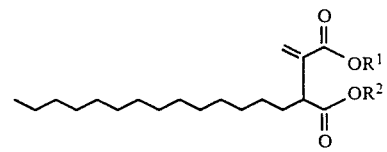

II wherein:
$R^1$ and $R^2$ are each independently selected from:
a) H;
b) $C_{1-5}$alkyl;
c) $C_{1-5}$alkyl substituted with a member of the group consisting of:
  i) phenyl,
  ii) phenyl substituted with methyl, methoxy, halogen (Cl, Br, F, I) or hydroxy; or a pharmaceutically acceptable salt of a compound of formula (I) in which at least one of $R^1$ and $R^2$ is hydrogen;

when $R^1$, $R^2$ is other than H, these compounds may not be inhibitors of farnesyl-protein transferase but may act as prodrugs.

A preferred compound (12) of this invention is set forth below:

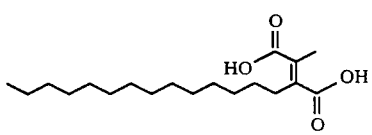

I

A preferred compound (10) of this invention is set forth below:

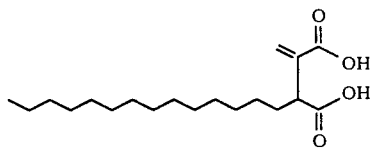

The pharmaceutically acceptable salts of the acids of the compounds of this invention are readily prepared by conventional procedures such as treating an acid of the compounds of this invention with an appropriate amount of a base, such as an alkali or alkaline earth metal hydroxide, e.g., sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

The compounds of this invention are prepared according to the reaction scheme as set forth below:

REACTION SCHEME

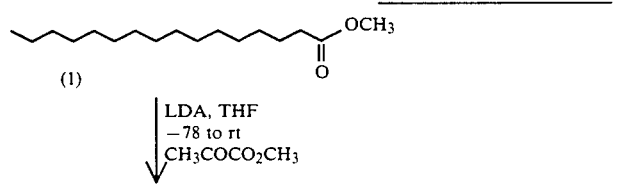

-continued
REACTION SCHEME

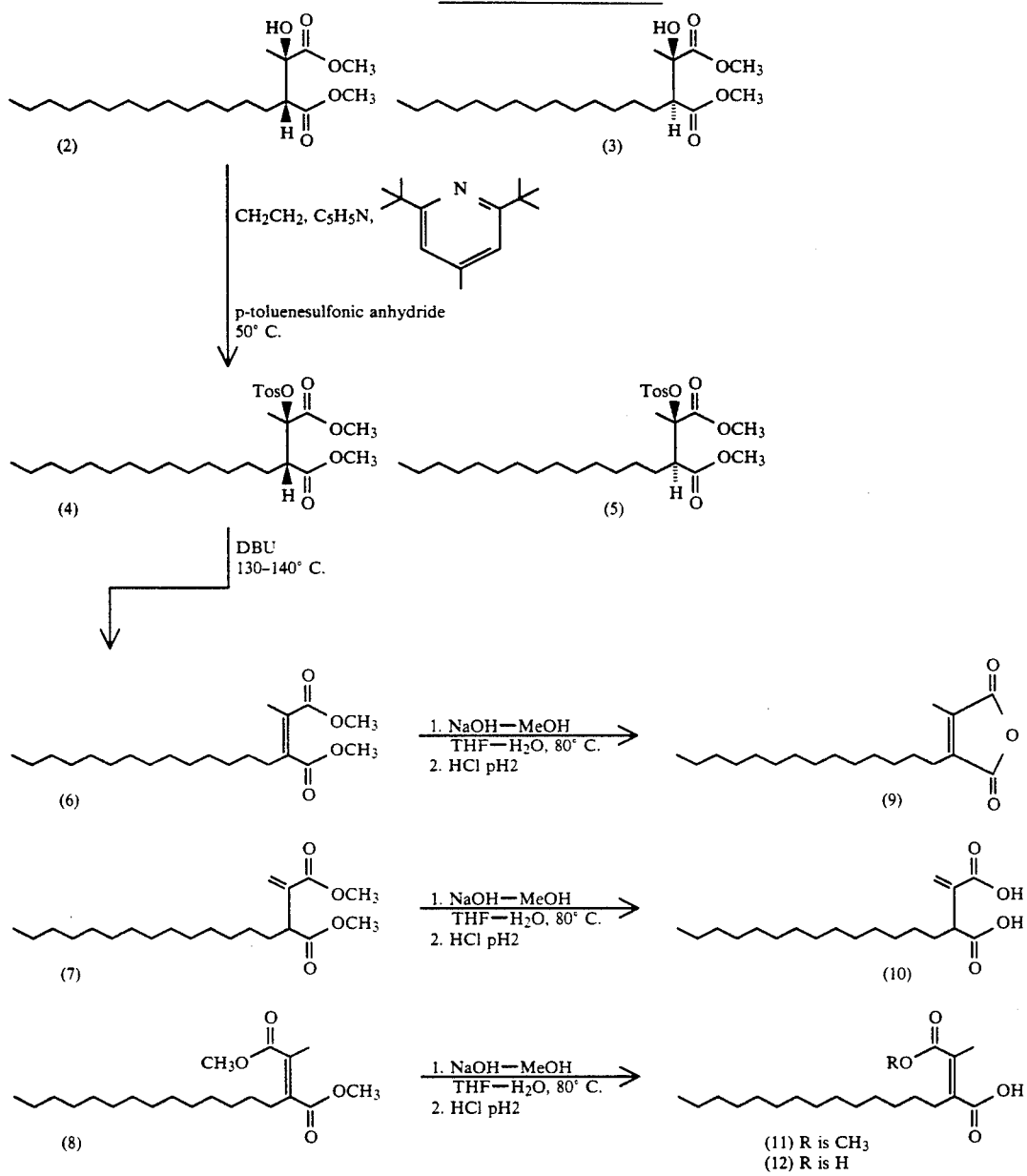

The pharmaceutical composition of the compounds of this invention can be used to inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of a chemotherapeutic compound according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a useful value pH, e.g., 7.4. The solutions may be introduced into a patient's intramuscular bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a human patient undergoing treatment for cancer. Administration occurs in an amount between about 0.1 mg/kg of body weight to about 20 mg/kg of body weight of a mammal per day, preferably of between 0.5 mg/kg of body weight to about 10 mg/kg of body weight of a mammal per day.

EXAMPLES

Examples provided are intended to assist in a further understanding of the invention. Particular materials employed, species and conditions are intended to be further illustrative of the invention and not limitative of the reasonable scope thereof.

EXAMPLE 1

Preparation of Compounds (10), (11) and (12) by Synthesis

Step 1: Aldol Condensation of Methyl Palmitate and Methyl Pyruvate (Preparation of (2) and (3))

n-Butyl lithium (1.6M in hexane, 6.6 mL, 10.5 mmol) was added to a cooled (−78° C.) solution of diisopropyl amine (2.2 mL, 15 mmol) in THF (10 mL). The solution was stirred under $N_2$ at −78° C. for 10 minutes followed by at 0° C. for 10 minutes. After cooling the LDA solution at −78° C., a THF (20 mL) solution of methyl palmitate (1) (2.7 g, 10 mmol) was added via a syringe over a 10 minute period and stirring was continued for 10 minutes. The reaction mixture was slowly allowed to warm to 0° C. and stirred for 30 minutes (faint yellow color). Methyl pyruvate (0.90 mL, 10 mmol) was added via a syringe after recooling the reaction mixture at −40° C. and solution was stirred for 1 hr while slowly warming to room temperature. Progress of the reaction was monitored on TLC (hexane-EtOAc, 4:1). Two polar products were formed. Some unreacted methyl palmitate was still present. The mixture was quenched with water at −78° C. and allowed to warm to room temperature, diluted with aqueous citric acid (100 mL) and extracted with ethyl acetate (3×100 mL). EtOAc extract was washed with water (100 mL), dried ($Na_2SO_4$), and evaporated under reduced pressure to give an oily material which was chromatographed on a flash silica gel (200 cc) column packed in hexane. The column was eluted with 5% EtOAc in hexane to afford 300 mg of the first diastereomer (2) or (3), HPLC, retention time 7.0 minutes, Whatman ODS-3, C-18 (4.6×250 mm), $CH_3OH$-$H_2O$, 92:8, [at a flow rate of 1.5 ml/min], 700 mg of mixture and 300 mg of second diastereomer (3) or (2), ret time 6.4 min). Both compounds were obtained as solids. The stereochemical identity of diastereomer (2) and (3) was not determined.

$^1$H NMR spectrum (2) or (3) (diastereomer with 7.0 min retention time) in $CDCl_3$: 3.75 (3H, s), 3.67 (3H, s), 2.76 (1H, dd, J=10.5, 3.9 Hz), 1.68 (2H, m), 1.41 (3H, s), 1.25 (24H, brm), 0.87 (3H, t, J=6.3 Hz).

$^1$H NMR spectrum (3) or (2) (diastereomer with 6.4 min retention time) in $CDCl_3$: 3.79 (3H, s), 3.71 (3H, s), 2.75 (1H, dd, J=11.7, 3.3 Hz), 1.83 (2H, m), 1.42 (3H, s), 1.23 (24H, m), 0.87 (3H, t, J=6.3 Hz).

Step 2: β-Elimination Reaction of Aldol Products (Preparation of Compounds (6), (7) and (8))

To a solution of 160 mg (0.43 mmol) of the diastereomere (2) or (3) with HPLC retention time 7.0 minute obtained in Step 1 above in $CH_2Cl_2$ (1.5 mL) and pyridine (10 mL) was added 2,6-di-tert-butyl-4-methylpyridine (200 mg, 0.97 mmol) followed by p-toluenesulfonic anhydride (570 mg, 1.74 mmol) and the solution was heated at 50° C. under $N_2$ overnight. Progress of the reaction was monitored on TLC (hexane-EtOAc, 85:15). The tosylate ** was less polar than starting alcohol. DBU (0.5 mL) was added and the reaction mixture was heated at 130°–140° C. for 3 hrs to give citraconic acid diester (ret time* 8.8 min, ∼50%), itaconic acid idester analog (ret time* 9.4 min, 40%) and mesaconic acid diester analog (ret time* 9.8 min, ∼10%).

Similarly, reaction of (3) or (2) (diastereomer with retention time 6.4 min.) (90 mg, 0.26 mmol) in $CH_2Cl_2$ (1.5 mL), pyridine (1 mL), 2,6-di-tert-butyl-4-methylpyridine (100 mg) with p-toluenesulfonic anhydride (270 mg) at 50° C. followed by heating with DBU for 20 min gave mesaconic acid diester with citraconate and itaconate dimethyl esters.

Both reaction mixtures were cooled to room temperature and worked up together, they were poured on to EtOAc (200 mL) and washed sequentially with 4N aqueous HCl (3×50 mL), water, 10% aqueous NaHCO$_3$ (3×50 mL) followed by water. The ethyl acetate extract was dried ($Na_2SO_4$), evaporated under reduced pressure and crude product was chromatographed on a flash silica gel column (100 cc) packed in hexane and eluted with initially 2% EtOAc followed by 3% to give citraconate analog (6) (80 mg), (7) 88 mg and (8) (25 mg). Combined yield 81%.

The tosylate could be purified on the silica gel column using 2 to 5% EtOAc in hexane. The mixture of aldol products could be used for the elimination reaction without any significant problem.

**$^1$H NMR spectrum (4) or (5) $CDCl_3$: 7.76 (2H, d, J=8.4 Hz), 7.32 (2H, d, J=8.4 Hz), 3.83 (3H, s), 3.67 (3H, s), 2.95 (1H, dd, J=11.7, 3.0 Hz), 2.44 (3H, s), 1.81 (3H, s), 1.60 (2H, m), 1.24 (24H, m), 0.88 (3H, t, J=6.0 Hz).

$^1$H NMR spectrum (6) $CDCl_3$: 3.75 (3H, s), 3.74 (3H, s), 2.32 (2H, t, J=7.2 Hz), 1.94 (3H, brs), 1.43 (2H, m), 1.24 (22H, m), 0.86 (3H, t, J=6.6 Hz).

$^1$H NMR spectrum (8) $CDCl_3$: 3.78 (3H, s), 3.77 (3H, s), 2.43 (2H, t, J=8.5 Hz), 1.99 (3H, brs), 1.40 (2H, m), 1.24 (22H, m), 0.87 (3H, t, J=6.8 Hz).

$^1$H NMR spectrum (7) $CDCl_3$: 6.35 (1H, s), 5.74 (1H, s), 3.76 (3H, s), 3.67 (3H, s), 3.49 (1H, t, J=7.2 Hz), 1.86 (1H, m), 1.65 (1H, m), 1.24 (24H, m), 0.87 (3H, t, J=6.3 Hz).

*HPLC condition, Whatman ODS-3 (C-18), 4.6×250 mm, $CH_3OH$-$H_2O$ (92:8), flow rate 1.5 ml/min.

Step 3: Hydrolysis of Citraconate Dimethyl Esters Analog (Preparation of Compound (9))

A solution of citraconate dimethyl ester analog (6) (40 mg) in THF (1 mL), methanol (1 mL), water (1 mL) and 4N NaOH (0.5 mL) was heated at reflux overnight and the progress of the reaction was monitored on HPLC*. After completion of the reaction it was cooled to 0° C. and acidified with 4N HCl to pH 2. The product was extracted with dichloromethane (2×25 mL). The $CH_2Cl_2$ solution was washed with water, dried ($Na_2SO_4$) and evaporated to give colorless product anhydride (ret time *8.9 min) which solidified upon cooling.

* Anal HPLC condition: Whatman C-18, 4.6×250 mm, $CH_3CN$-$H_2O$, 90:10 (containing 0.2% TFA), flow rate 1.5 ml/min.

Step 4: Hydrolysis of Mesaconate Dimethyl Ester Analog (8) (Preparation of Compounds (11) and (12))

Using conditions described above mesaconate analog (8) was hydrolyzed for 30 minutes to give mono-methyl ester (11), ret time* 12.2 min) with a trace of diacid (12), ret time 5.8 min). Refluxing of the reaction mixture overnight gave diacid (quantitative). The mono-methyl ester was purified on a prep PPLC column (Whatman C-18, 22×250 mm, flow rate 10 ml/min, $CH_3CN$ (65%), $H_2O$ (35% containing 0.8% TFA). The location of methyl ester group in (11) was confirmed by NMR using LR $^1H$-$^{13}C$ COSY experiment. $^1H$ NMR spectrum (11) $CDCl_3$: 3.81 (3H, s), 2.58 (2H, t, J=7.5 Hz), 2.00 (3H, s), 1.43 (2H, m), 1.24 (22H, m), 0.88 (3H, t, J=6.7 Hz).

$^1H$ NMR spectrum (12) $CDCl_3$: 2.58 (2H, t, J=7.8 Hz), 2.14 (3H, m), 1.52 (2H, m), 1.26 (22H, m), 0.89 (3H, t, J=6.6 Hz).

* Anal HPLC condition: Whatman C-18, (4.6×250 mm,) $CH_3CN$ (80%): $H_2O$ (20%) containing 0.8% TFA), flow rate 1.5 ml/min.

Step 5: Hydrolysis of Itaconate Dimethyl Ester Analog (7) (Preparation of Compound (10))

Itaconate diester (7) (50 mg) was hydrolyzed following the conditions described for citraconic acid. As expected, the hydrolysis gave a mixture of itaconic acid analog (10) (ret time* 7.7 min, 72%, powder), citraconic anhydride analog (9) (ret time* 12.9 min, ~20%) and mesaconic acid analog (12) ret time* 5.9 min, 8%, powder) over all yield ~80%. These acids were purified on a prep HPLC column [Whatman C-18, 22×250 mm, gradient elution with $CH_3CN$-$H_2O$ (containing 1% TFA) 65:35 to 75:25 over 60 minutes followed by 90:10 at a flow rate 10 ml/min].

$^1H$ NMR spectrum of (10) in $CDCl_3$: 6.52 (1H, s), 5.82 (1H, s), 3.37 (1H, t, J=7 Hz), 1.93 (1H, m), 1.73 (1H, m), 1.25 (24H, m), 0.83 (3H, t, J=6.6 Hz).

*Anal HPLC condition: Whatman C-18 (4.6×250 mm), $CH_3CH$ (80%): $H_2O$ (20% containing 0.8% TFA), flow rate 1.5 ml/min.

EXAMPLE 2

In Vitro Inhibition of Ras Farnesyl Transferase

Farnesyl-protein transferase (FTase) from bovine brain was chromatographed on DEAE-Sephacel (Pharmacia, 0-0.8M NaCl gradient elution), N-octyl agarose (Sigma, 0-0.6M NaCl gradient elution), and a mono Q HPLC column (Pharmacia, 0-0.3M NaCl gradient). Ras-CVLS at 3.5 μM, 0.25 μM [$^3H$]FPP, and the indicated compounds were incubated with this partially purified enzyme preparation. The FTase inhibitory data presented below is a measurement of the ability of the test compound to inhibit Ras farnesylation in vitro.

TABLE 1

| Inhibition of Ras farnesylation by compounds of this invention | |
|---|---|
| Compound | $IC_{50}$ (uM) |
| A | 7.7 |
| B | 1.7 |

*($IC_{50}$ is the concentration of compound which gives 50% inhibition of FTase under the described assay conditions)

EXAMPLE 3

As a specific embodiment of an oral composition of a compound of this invention, 20 mg of compounds (10), (11) or (12) is formulated with sufficient finely divided lactose to provide a total amount of 580 to 590 mg to fill a size 0 hard gelatin capsule.

EXAMPLE 4

Preparation of an Ammonium Salt

A 0.1 mmol sample of the free acid of compounds (11) or (12) is dissolved in 10 ml of ethyl acetate. The resulting solution is saturated with gaseous ammonia and evaporated to leave the ammonium salt.

EXAMPLE 5

Preparation of a Potassium Salt

A solution of 0.1 mmol of the free acid of compounds (10), (11) or (12) in 10 ml of 6:4 methanol/water is treated with an aqueous or methanolic solution containing 0.1 or 0.2 mmol of potassium hydroxide. Evaporation of the solvent afforded corresponding potassium salt. Addition of between 0.1 and 0.2 mmol of potassium hydroxide yields analogously mixtures of the mono-potassium and di-potassium and salts whose composition depends upon the exact amount of potassium hydroxide added. In a similar fashion the sodium and lithium salts can be formed.

EXAMPLE 6

Preparation of a Calcium Salt

A solution of 0.1 mmol of the free acid of compound (10) in 20 ml of 6:4 methanol/water is treated with an aqueous solution of 0.1 mmol of calcium hydroxide. The solvents are evaporated to give the corresponding calcium salt.

EXAMPLE 7

Preparation of an Ethylenediamine Salt

A solution of 0.1 mmol of compounds (10), (11) or (12) in 10 ml of 6:4 methanol/water is treated with 0.1 mmol of ethylenediamine. Evaporation of the solvent affords the ethylenediamine salt. The procedure can also be applied to the preparation of the N,N"-dibenzylethylenediamine salt.

EXAMPLE 8

Preparation of a Tris(hydroxymethyl)aminomethane Salt

To a solution of 0.1 mmol of compounds (10), (11) or (12) in 10 ml of 6:4 methanol/water is added from 0.1 to 0.2 mmol of tris(hydroxymethyl)-aminomethane dissolved in 10 ml of methanol. Evaporation of the solvent gives a corresponding salt form of Compounds (10),

(11) or (12), the exact composition of which is determined by the molar ratio of amine added. Similarly prepared are the salts of L-ornithine, L-lysine, and N-methylgluacamine.

EXAMPLE 9

Preparation of an L-arginine Salt

A solution of 0.1 mmol of the free acid of compounds (10), (11) or (12) in 10 ml of 6:4 methanol/water is treated with an aqueous solution of 0.1 to 0.2 mmol of L-arginine. Evaporation of the solvent affords the title salt, the exact composition of which is determined by the molar ratio of amino acid to the free acid of compounds (10), (11) or (12) used. Similarly prepared are the salts of L-ornithine, L-lysine and N-methylglucamine.

What is claimed is:

1. A compound which inhibits farnesyl-protein transferase of the formula:

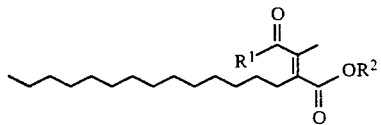

I wherein:
 $R^1$ and $R^2$ are each independently selected from:
 a) H;
 b) $C_{1-5}$alkyl;
 c) $C_{1-5}$alkyl substituted with a member of the group consisting of:
  i) phenyl,
  ii) phenyl substituted with methyl, methoxy, halogen (Cl, Br, F, I) or hydroxy; or a pharmaceutically acceptable salt of a compound of formula (I) in which at least one of $R^1$ and $R^2$ is hydrogen;
 when $R^1$, $R^2$ is other than H, these compounds may not be inhibitors of farnesyl-protein transferase but may act as prodrugs.

2. A compound according to claim 1 which is:

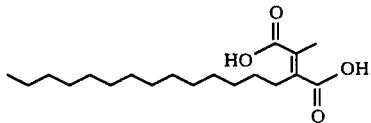

3. A chemotherapeutic composition comprising a pharmaceutical carrier, and dispersed therein, a therapeutically effective amount of a compound of claim 1.

* * * * *